United States Patent [19]

Kamiya et al.

[11] 4,237,305
[45] Dec. 2, 1980

[54] SUBSTITUTED PHENYLACETIC ACID COMPOUNDS AND PROCESS FOR PREPARATION THEREOF

[75] Inventors: Takashi Kamiya, Suita; Masashi Hashimoto, Toyonaka; Osamu Nakaguti, Nagaicho-Higashi; Teruo Oku, Osaka; Hidekazu Takeno, Kita, all of Japan

[73] Assignee: Fujisawa Pharmaceutical Co., Ltd., Osaka, Japan

[21] Appl. No.: 782,968

[22] Filed: Mar. 30, 1977

[30] Foreign Application Priority Data

Mar. 30, 1976 [JP] Japan ................... 51/35600

[51] Int. Cl.$^3$ .................... C07C 125/065
[52] U.S. Cl. .................... 560/29; 260/239 A; 260/326 A; 260/345.7 R; 260/465 D; 546/153; 546/247; 546/335; 560/35; 560/53; 562/444; 562/464; 556/413; 556/441
[58] Field of Search ................... 560/29

[56] References Cited

U.S. PATENT DOCUMENTS

| 3,852,290 | 12/1974 | Nagasawa et al. | 560/32 |
| 3,875,207 | 4/1975 | Iselin et al. | 560/29 |
| 3,891,692 | 6/1975 | Veber et al. | 560/32 |
| 3,923,977 | 12/1975 | Aoki et al. | 260/239 A |

FOREIGN PATENT DOCUMENTS 830934  1/1976  Belgium ................... 560/29

OTHER PUBLICATIONS

Hashimoto et al., J.A.C.S., 98(10), 3023–3025, 1976.
Wagner & Zook, Synthetic Organic Chem., John Wiley & Sons, Inc., pp. 565–573 & 585–589, (1965).
McOmie, Protective Groups in Organic Chem., Plenum Press, pp. 58–59, 86–87, 185–187, 210–211, (1973).

Primary Examiner—Natalie Trousof
Assistant Examiner—G. T. Breitenstein
Attorney, Agent, or Firm—Dayton R. Stemple, Jr.

[57] ABSTRACT

Substituted phenylacetic acid compounds represented by the following general formula and preparation thereof:

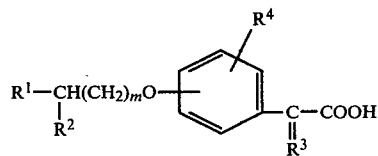

wherein
$R^1$ is hydrogen or protected carboxy,
$R^2$ is hydrogen, or protected amino, provided that when $R^1$ is hydrogen, then $R^2$ is protected amino, and when $R^2$ is hydrogen, then $R^1$ is protected carboxy,
$R^3$ is oxo, hydroxyimino or protected hydroxyimino,
$R^4$ is hydrogen or halogen, and
m is an integer of 1 to 3.

7 Claims, No Drawings

SUBSTITUTED PHENYLACETIC ACID COMPOUNDS AND PROCESS FOR PREPARATION THEREOF

BACKGROUND OF THE INVENTION

This invention relates to novel substituted phenylacetic acid compounds which are useful as an acylating agent for preparing 3-acylamino-2-azetidinone compounds, especially, Nocardicin A having the following formula:

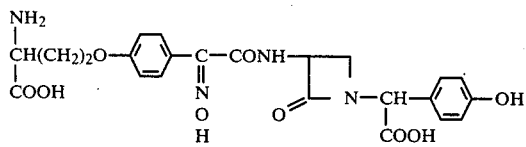

Nocardicin A is valuable antibiotic especially against pathogenic Pseudomonas species and first produced by fermentation, and U.S. patent application covering the same was filed under Ser. No. 458,211 and granted under U.S. Pat. No. 3,923,977.

Further, U.S. patent application covering 3-acylamino-2-azetidinone compounds was filed on July 7, 1975 under Ser. No. 593,668 which is now abandoned, and C.I.P. application of it was filed on June 10, 1976 under Ser. No. 694,891, now abandoned. In the specification of said U.S. patent application Ser. No. 593,668, there are disclosed many 3-acylamino-2-azetidinones and an acylation process for preparation thereof. However in said specification, any specific object compounds per se of this invention are not disclosed as acylating agent, although the object compounds of this invention is only generically or subgenerically disclosed without specific descriptions therein.

Furthermore, in the prior specification, there are disclosed a few 3-acylamino-2-azetidinone compounds prepared by acylation of 3-amino-2-azetidinone compounds with the acylating agent which is structurally-close to the object compounds of this invention (see Example Nos. 96 and 97 of U.S. patent application Ser. No. 694,891). However, these compounds (i.e. Example Nos. 96 and 97), can not be used as a synthetic intermediate for Nocardicin A because the α-methoxyimino function of their 3-acyl groups can hardly be transformed into hydroxyimino function without any undesired degradations of their foundamental molecules such as cleavage of 2-azetidinone ring, elimination of 3-acyl group, etc.

Under the above state of prior art, in order to prepare Nocardicin A and other analogous compounds by chemical synthesis, inventors of this invention have investigated extensively and resulted successfully in synthesizing a useful starting acylating agent (i.e. object compounds of this invention) for preparing Nocardicin A and the other analogues.

Accordingly, the object compounds of this invention are characterized by substituted phenylacetic acid compounds having a protected amino group and/or a protected carboxy group, there protective groups of which are capable of being easily eliminated under mild reaction conditions.

The above successful synthesis of the substituted phenylacetic acid compounds thus realized have firstly provided new preparation method of Nocardicin A by chemical synthesis in addition to the prior fermention method.

DETAILED DESCRIPTION OF THE PREFERRED EMBODIMENTS OF THE INVENTION

This invention relates to new substituted phenylacetic acid compounds which are useful as starting acylating agents for preparing 3-acylamino-2-azetidinone compounds, especially Nocardicin A.

Accordingly, it is an object of this invention to provide new substituted phenylacetic acid compounds which are useful starting acylating agents for preparing 3-acylamino-2-azetidinone compounds, especially Nocartidin A.

Another object of this invention is to provide processes for preparation of said new substituted phenylacetic acid compounds.

SUBSTITUTED PHENYLACETIC ACID COMPOUNDS

The object compound of this invention, substituted phenylacetic acid compounds, is represented by the following general formula:

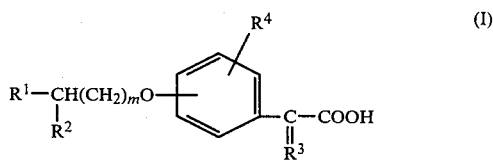

wherein
$R^1$ is hydrogen or protected carboxy,
$R^2$ is hydrogen, or protected amino, provided that when $R^1$ is hydrogen, then $R^2$ is protected amino, and when $R^2$ is hydrogen, then $R^1$ is protected carboxy,
$R^3$ is oxo, hydroxyimino or protected hydroxyimino,
$R^4$ is hydrogen or halogen, and
m is an integer of 1 to 3

REACTION SCHEMES OF THE PROCESS FOR THE PREPARATION OF THE OBJECT COMPOUNDS

According to this invention, the object compounds (I) can be prepared by the processes according to the following reaction schemes:

(1) Process 1:

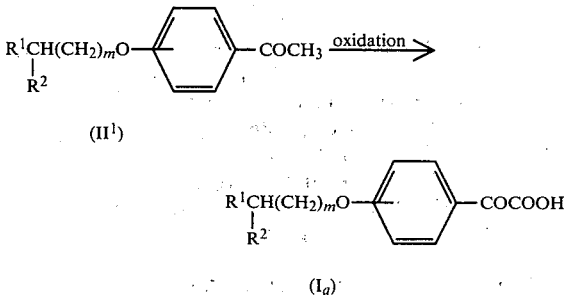

wherein $R^1$, $R^2$ and m are each as defined above.
(2) Process 2:

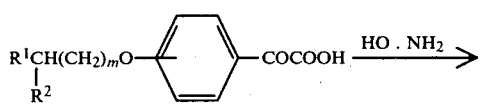

(Iₐ)

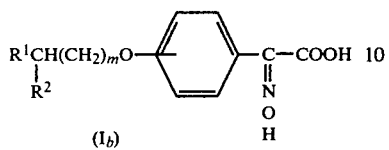

(I_b)

wherein $R^1$, $R^2$ and m are each as defined above.

(3) Process 3:

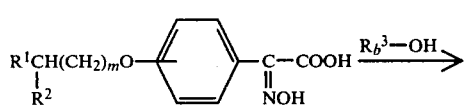

(I_b)

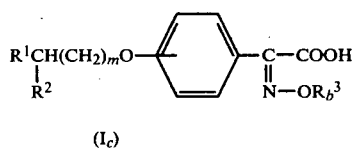

(I_c)

wherein $R^1$, $R^2$ and m are each as defined above, and $R_b^3$ is acyl.

(4) Process 4:

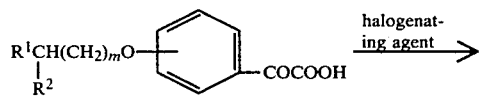

(Iₐ)

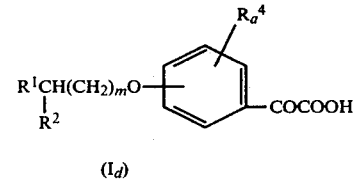

(I_d)

wherein $R^1$, $R^2$ and m are each as defined above, and $R_a^4$ is halogen.

Particulars of the above definitions and preferred examples thereof are explained as follows:

(1) Re: Protected carboxy for $R^1$

As preferred examples of protected carboxy, there may be exemplified by an ester such as silyl ester, aliphatic ester and esters containing an aromatic or a heterocyclic group. The suitable silyl esters include trialkylsilyl (e.g. trimethylsilyl, triethylsilyl, etc.) esters, haloalkylsilyl (e.g. chloro-dimethylsilyl, dichloro-methylsilyl, etc.) ester, trihalosilyl (e.g. trichlorosilyl, etc.) ester, alkylalkoxysilyl (e.g. methyl-diethoxysilyl, etc.) ester, trialkoxysilyl (e.g. tris(2-chloroethoxy)silyl, etc.) ester, and the like.

Suitable aliphatic esters include: alkyl (e.g. methyl, ethyl, propyl, isopropyl, butyl, tert-butyl, etc.) esters; cycloalkyl (e.g. cyclopentyl, cyclohexyl, etc.) esters; and the like.

Suitable esters containing an aromatic group include, for example, aryl (e.g. phenyl, tolyl, xylyl, etc.) esters; aralkyl (e.g. benzyl, phenethyl, etc.) esters; aryloxyalkyl (e.g. phenoxymethyl, phenoxyethyl, etc.) esters; aroylalkyl (e.g. phenacyl, toluoylethyl, etc.) esters; and the like.

Suitable esters containing heterocyclic group include: heterocyclic esters, heterocyclic-alkyl esters, etc.; in which the suitable heterocyclic ester include saturated or unsaturated, monocyclic or fused, 3 to 10-membered heterocyclic group containing 1 to 4 heteroatom(s) such as an oxygen, sulfur and nitrogen atom, (e.g. pyridyl, piperidinyl, 2-pyridon-1-yl, tetrahydropyranyl, quinolyl, pyrazolyl, etc.) esters; and the like, and the suitable hetrocyclic-alkyl esters include, for example, aforementioned heterocyclic group-substituted-alkyl (e.g. pyridylmethyl, furfuryl, 4-methylpiperazinoethyl, etc.) esters; and the like.

In the silyl esters, the aliphatic esters and the esters containing an aromatic or heterocyclic group as mentioned above, the moiety of these esters may optionally have one or more appropriate substituent(s) such as alkyl (e.g. methyl, ethyl, etc.), cycloalkyl (e.g. cyclopropyl, cyclohexyl, etc.), alkoxy (e.g. methoxy, ethoxy, etc.), alkanoyloxy (e.g. acetoxy, etc.), alkylthio (e.g. methylthio, etc.), halogen (e.g. chlorine, etc.), cyano, nitro, etc. Examples of such substituted esters may be mono-(di or tri)haloalkyl (e.g. chloromethyl, bromoethyl, dichloromethyl, 2,2,2-trichloroethyl, 2,2,2-tribromoethyl, 2,2,2-trifluoroethyl, etc.) esters, cyanoalkyl (e.g. cyanomethyl, cyanoethyl, etc.) esters, cycloalkyl-substituted-alkyl (e.g. 1-cyclopropylethyl, etc.) ester, mono(di, tri, tetra or penta)halophenyl (e.g. 4-chlorophenyl, 3,5-dibromophenyl, 2,4,5-trichlorophenyl, 2,4,6-trichlorophenyl, pentachlorophenyl, etc.) esters, and the like.

(2) Re: Protected amino for $R^2$

As preferred examples of protected amino, there may be exemplified by acylamino group, such as substituted or unsubstituted alkoxycarbonyl (e.g. methoxycarbonyl, ethoxycarbonyl, propoxycarbonyl, butoxycarbonyl, tert-butoxycarbonyl, chloromethoxycarbonyl, bromoethoxycarbonyl, tribromoethoxycarbonyl, trichloroethoxycarbonyl, etc.)amino, substituted or unsubstituted aralkoxycarbonyl (e.g. benzyloxycarbonyl, phenethyloxycarbonyl, diphenylmethoxycarbonyl, nitrobenzyloxycarbonyl, bromobenzyloxycarbonyl, methoxybenzyloxycarbonyl, dinitrobenzyloxycarbonyl, etc.)amino, or halogenated alkanoyl (e.g. trifluoroacetyl, etc.)amino;

substituted or unsubstituted aralkyl (e.g. benzyl, diphenylmethyl, trityl, bromobenzyl, nitrobenzyl, etc.) amino;

substituted or unsubstituted arylthio (e.g. phenylthio, nitrophenylthio, dinitrophenylthio, etc.)amino;

substituted or unsubstituted alkylidene (e.g. ethylene, isopropylidene, 2-carboxyisopropylidene, etc.) amino or its tautomeric 1-alkenyl (e.g. 2-methoxycarbonyl-1-methylvinyl, etc.)amino;

aralkylidene (e.g. benzylidene, salicylidene,etc.) amino;

and the like.

Among these protected amino as mentioned above, more preferred protected amino may be acyl amino group, and furthermore preferred ones are substituted or unsubstituted aralkoxycarbonylamino groups as particularly exemplified as above, and the most preferred one may be alkoxycarbonylamino (e.g. tert-butoxycarbonylamino, etc.).

(3) Re: Protected hydroxyimino for $R^3$

As preferred examples of protected hydroxyimino, there may be exemplified acyloxyimino such as alkanoyloxyimino (e.g. acetoxyimino, propionyloxyimino, isopropionyloxyimino, butyryloxyimino, pentanoyloxyimino, etc.), haloalkanoyloxyimino (e.g. chloroacetoxyimino, di-chloroacetoxyimino, trichloroacetoxyimino, bromo-acetoxyimino, trifluoroacetoxyimino, di-chloropropionyloxyimino, etc.), substituted or unsubstituted aroyloxyimino (e.g. benzoyloxyimino, toluoyloxyimino, xyloyloxyimino, naphthoyloxyimino, 4-nitrobenzoyloxyimino, 4-methoxybenzoyloxyimino, 2,4,6-trichlorobenzoyloxyimino, etc.) and the like.

And, regarding acyl for $R_b{}^3$, preferred examples may be the acyl moiety of the acyloxyimino as mentioned above for protected hydroxyimino for $R^3$.

(4) Re: Halogen for $R^4$ and $R_a{}^4$

As preferred examples of halogen for $R^4$, there may be exemplified fuluorine, chlorine, bromine and iodine, among which chlorine is preferred.

DETAILED EXPLANATION OF PROCESSES FOR PREPARATION OF THE OBJECT COMPOUNDS (1) Process 1

This process relates to one for preparing the compound ($I_a$) by oxidizing the compound ($II^1$) with an oxidizing agent.

The oxidizing agent to be used in this reaction is conventional one which is capable of oxidizing an acetyl group to the corresponding oxalo group, and accordingly preferred examples of such oxidizing agents may be selenium dioxide; permanganate such as potassium permanganate and the like; a combination of nitrite such as sodium nitrite, and an inorganic acid such as hydrochloric acid and sulfuric acid, etc.

The oxidation is usually carried out in a solvent such as water, ether, benzene, pyridine, dioxane, the other conventional ones which do not affect adversely to the reaction or an optional mixture thereof, and the reaction is preferably, at ambient temperature or at an elevated temperature.

(2) Process 2

This process relates to one for preparing the compound ($I_b$) by reacting the compound ($I_a$) with hydroxylamine or a salt thereof.

Suitable salt of hydroxylamine includes an inorganic acid salt (e.g. hydrochloride, hydrobromide, sulfate, etc.) or an organic acid salt (e.g. formate, acetate, 2,2,2-trifluoroacetate, p-toluenesulfonate, etc.). In such case, the reaction may be preferably conducted in the presence of a base. Suitable base may be an inorganic base such as alkali or alkaline earth metal hydroxide (e.g. sodium hydroxide, potassium hydroxide, calcium hydroxide, sodium bicarbonate, etc.), alkali metal bicarbonate (e.g. sodium bicarbonate, potassium bicarbonate, etc.), alkali or alkaline earth metal carbonate (e.g. sodium carbonate, calcium carbonate, etc.), alkali metal phosphate (e.g. sodium dihydrogenphosphate, potassium dihydrogenphosphate, disodium hydrogenphosphate, dipotassium hydrogenphosphate, etc.) or an organic base such as alkali metal alkoxide (e.g. sodium methoxide, potassium ethoxide, etc.), amines (e.g. triethylamine, pyridine, lutidine, etc.).

The reaction is usually conducted in conventional manner. For example, the reaction is preferably conducted under cooling, at ambient temperature or under heating, and in conventional solvent which does not have an adverse influence on the reaction such as water, methanol, ethanol, propanol, N,N-dimethylformamide or an optional mixture thereof.

(3) Process 3

This process relates to one for preparing the compound ($I_c$) by reacting the compound ($I_b$) with a carboxylic acid of the formula: $R_b{}^3$—OH wherein $R_b{}^3$ is acyl, or its reactive derivatives.

The carboxylic acid of the formula $R_b{}^3$—OH includes aliphatic and aromatic carboxylic acids, and more preferred examples thereof may include the ones which have the same acyl moiety as those exemplified in the explanation of protected hydroxyimino for $R^3$ hereinabove.

The reactive derivatives of these carboxylic acids include conventional ones such as acid halides (e.g. acid chloride, acid bromide etc.), activated amides (e.g. pyrazole, imidazole etc.), activated esters (e.g. cyanomethyl ester methoxymethyl ester, etc.), acid azides, acid anhydrides, mixed acid anhydrides with other acids, including carboxylic, carbonic, sulfonic, phosphoric acids etc., and the like.

The reaction is usually carried out in a conventional solvent such as water, acetone, dioxane, acetonitrile, dichloromethane, chloroform, ethylene chloride, tetrahydrofuran, ethyl acetate, diethyl ether, benzene, toluene, pyridine, N,N-dimethylformamide, etc. and an optional mixture thereof.

When a free carboxylic acid or a salt thereof is employed in this reaction, the reaction is preferably carried out in the presence of a condensing agent conventionally used in a similar reaction to this.

This reaction is usually carried out under mild conditions such as under cooling or an elevated temperature.

(4) Process 4

This process relates to one for preparing the compound ($I_d$) by reacting the compound ($I_a$) with a halogenating agent.

Preferred examples of such halogenating agents may include halogen such as chlorine, bromine, etc. hypohalogenous acid or a salt or ester thereof such as hypochlorous acid, hypobromus acid, sodium hypochlorite, tert-butylhypochlorite etc.; N-haloamide such as 1,3,5-trichloroisocyanuric acid, N-bromoacetamide, N-iodoacetamide, N-bromosuccinamide, N-chlorosuccinimide, N-chlorophtahlimide, etc.; a cuprous halogenide such as cuprous chloride, cuprous bromide, etc.; and, pyridinium hydrobromide perbromide, dioxane dibromide, etc., and the like.

The reaction is usually carried out in an inert solvent. A suitable solvent to be used in this reaction may include any solvent which does not have adverse influence on the reaction, for example, water, methanol, ethanol, acetic acid, chloroform, methylene chloride, carbon tetrachloride, dioxane, acetonitrile, tetrahydrofuran, dimethylformamide and the like.

There is no limitation to the present reaction temperature, and the reaction is usually conducted under cooling, at ambient temperature or at somewhat elevated temperature.

STARTING COMPOUNDS OF THIS INVENTION AND THE INTERMEDIATES THEREOF

The starting compounds of this invention and intermediates thereof are represented by the following formula:

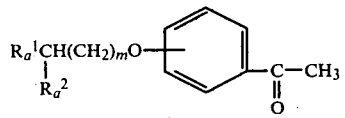

(II)

wherein
$R_a^1$ is hydrogen, halogen, carboxy or protected carboxy,
$R_a^2$ is hydrogen, amino or protected amino, and
m is an integer of 1 to 3.

Preparation of the starting compounds of this invention and the intermediate thereof can be illustrated as follows:

Acetophenon compounds (II$_a$), (II$_b$) and (II$_c$) can be prepared according to the following preparations A, B and C, respectively.

Preparation A

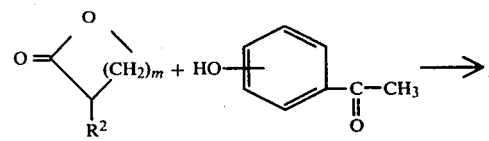

(III)    (IV)

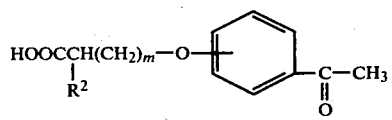

(II$_a$)

wherein
$R^2$ and m are each as defined above.
α-Phthalimide-γ-butyrolacton, compound (III), wherein
$R^2$ is phthalimido and m is 2, can be prepared according to the method as described in Canadican J. Chem. Vol. 36, page 593 (1958), and accordingly the other α-protected amino lactones, compound (III), wherein
$R^2$ is protected amino and m is 1 to 3, can also be prepared in the similar manner thereto. A hydroxy acetophenone (IV) can be prepared according to the method as described in Org. Reactions, Vol I, page 342 (John Wily & Sons, New York), and they are also available commercially.

Preparation B

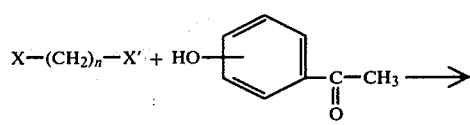

(V)    (IV)

[diagram of (II$_b$)]

wherein X and X' are each halogen, and n is an integer of 2 to 4.

Preparation C

[diagram showing phthalimide NH + X—(CH$_2$)$_n$O—C$_6$H$_4$—C(O)CH$_3$ (II$_b$) → phthalimide-N—(CH$_2$)$_n$O—C$_6$H$_4$—C(O)CH$_3$ (II$_c$)]

wherein X and n are each as defined above.

The other acetophenone compounds (II$_e$), (II$_f$) and (II$_h$) can be prepared according to the following Preparations, D, E and F, respectively.

Preparation D

[diagram showing $R_b^1$CH(CH$_2$)$_m$O—C$_6$H$_4$—C(O)CH$_3$ with phthalimide group, (II$_d$), with Removal of protective group of protected amino →]

[diagram showing $R_b^1$CH(CH$_2$)$_m$O—C$_6$H$_4$—C(O)CH$_3$ with NH$_2$, (II$_e$)]

wherein $R_b^1$ is hydrogen, carboxy or protected carboxy, and m is as defined before.

Preparation E

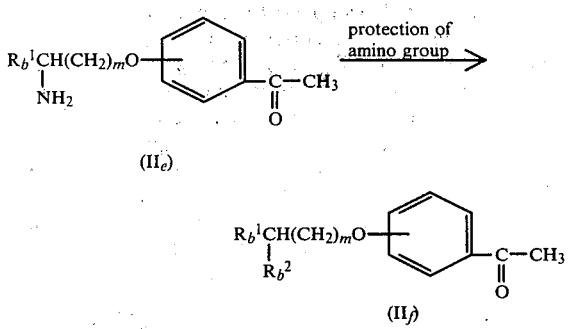

wherein
$R_b^1$ and m are each as defined above, and
$R_b^2$ is protected amino other than phthalimido.

Preparation F

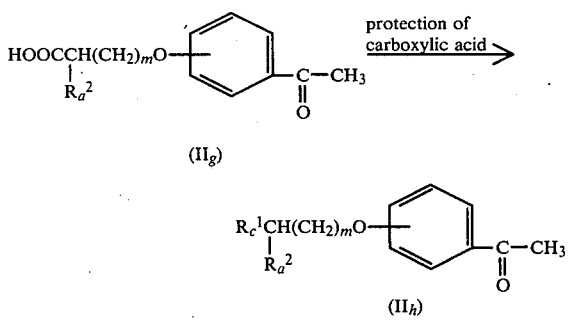

wherein
$R_c^1$ is protected carboxy,
$R_a^2$ and m are each as defined above.

Particulars of the above definitions (i.e. halogen, protected carboxy and protected amino) and preferred examples thereof are the same as those given in the explanation for Object Compound (I).

DETAILED EXPLANATION OF PROCESSES FOR PREPARATION OF THESE STARTING COMPOUNDS

Preparation A

This process relates to one for preparing the compound ($II_a$) by reacting the compound (III) with the compound (IV).

This reaction is preferably carried out in the presence of a base, preferred examples of which include the same as those given in the explanation for Process 2.

This reaction is usually carried out in a solvent, preferred examples of which include any conventional solvent which do not have an adverse influence on the reaction, for example, dioxane, bis(2-methoxyethyl) ether.

This reaction is preferably carried out at an ambient temperature or an elevated temperature.

Preparation B

This process relates to one for preparing the compound ($II_b$) by reacting the compound (IV) with the compound (V).

This reaction is preferably carried out in the presence of a base, preferred examples of which include the same as those given in the explanation for Process 2.

This reaction is usually carried out in a solvent such as acetone, methanol, ethanol and the like, under mild conditions such as under cooling or at an elevated temperature.

Preparation C

This process relates to one for preparing the compound ($II_c$) by reacting the compound ($II_b$) with phthalimide or its an alkali metal salt.

Preferred examples of such an alkali metal salt of phthalimide may include sodium salt, potassium salt and the like.

This reaction is usually carried out in any conventional solvent such as dimethylformamide, methanol, ethanol and the like.

In case that phthalimide per se is used in this process, the reaction is preferably carried out in the presence of a strong base such as an alkoxide, hydride or amide of alkali metal (e.g., sodium methoxide, potassium ethoxide, sodium hydride, sodium amide, etc.) and the like.

This reaction is usually carried out under mild conditions such as under cooling and at an elevated temperature.

Preparation D

This process relates to one for preparing the compound ($II_e$) by removing the phthaloyl of the phthalimido of the compound ($II_d$).

The removal of phthaloyl group is conducted by a conventional method such as hydrolysis including aminolysis, hydrazinolysis, etc., and other conventional method, e.g., a successive method comprising iminohalogenation, iminoetherification and hydrolysis.

In each of the above methods, suitable reagents to be used are exemplified as follows.

(i) For hydrolysis which refers to the same meaning as solvolysis including, for example, aminolysis, hydrozinolysis, etc.

Hydrolysis is preferably carried out in the presence of a base.

Suitable base is an inorganic base such as alkali or alkaline earth metal hydroxide, carbonate or bicarbonate (e.g. sodium hydroxide, potassium carbonate, sodium bicarbonate, calcium hydroxide, magnesium hydroxide, etc.), ammonium hydroxide and the like; an organic base such as an alkoxide or phenoxide of the above metal (e.g. sodium ethoxide, sodium methoxide, lithium phenoxide, etc.), an amine such as mono-, di- or trialkylamine (e.g. methylamine, ethylamine, propylamine, isopropylamine, butylamine, N,N-dimethyl-1,3-propanediamine, trimethylamine, triethylamine, etc.), unsubstituted, mono- or disubstituted arylamine (e.g. aniline, N-methylaniline, N,N-dimethylaniline, etc.) or a heterocyclic base (e.g. pyrrolidine, morpholine, N-methylmorpholine, N-methylpiperidine, N,N-dimethylpiperazine, pyridine, etc.), hydrazines (e.g. hydrazine, methylhydrazine, ethylhydrazine, etc.), a basic ion exchange resin and the like.

The hydrolysis is preferably conducted under cooling to elevated temperature and usually in conventional solvent such as water, methanol, ethanol, propanol, N,N-dimethylformamide, tetrahydrofuran, dioxane, dimethylsulfoxide, benzene, diethyl ether, etc.

(ii) For the successive method:

In this process, when the protected amino is an organic carboxamide group, the carboxamide bond can be more preferably cleaved by the following modified hydrolysis. That is, the compound ($II_d$) is first subjected to iminohalogenation, iminoetherification, and then hydrolysis. The first and second steps of this method are preferably carried out in an anhydrous condition at rather lower temperature. Suitable solvent for the first step (i.e. iminohalogenation) is an aprotic solvent such as dichloromethane, chloroform, diethyl ether, dioxane, etc., and for the second step (i.e. iminoetherification) is usually the same as those in the above first step. These two steps and the last step (i.e. hydrolysis step) are most preferably conducted in one-batch system.

Suitable iminohalogenation agents includes a halogenated compound such as phosphorus compound (e.g. phosphorus trichloride, phosphorus pentachloride, phosphorus tribromide, phosphorus pentabromide, phosphorus oxychloride, etc.), thionyl chloride, phosgene, and the like.

Suitable iminoetherifying agent may be an alcohol such as an alkanol (e.g. methanol, ethanol, propanol, isopropanol, butanol, tert-butyl alcohol, etc.) or an alkoxyalkanol (e.g. methoxyethanol, ethoxyethanol, etc.), a thiol such as alkane thiol (e.g. methane thiol, ethane thiol, etc.), the alkoxide or thiolate of a metal such as alkali metal, alkaline earth metal (e.g. sodium methoxide, potassium ethoxide, magnesium ethoxide, lithium methoxide, potassium methanethiolate, etc.), and the like. Thus obtained reaction product is, if necessary, hydrolyzed in a conventional manner. The hydrolysis is preferably carried out at ambient temperature or under cooling by simply mixing the reaction mixture with water or a hydrous or moistened organic solvent such as alcohol (e.g. methanol, ethanol, etc.), acetone, etc. and if necessary, with addition of an acid or base as exemplified above.

Preparation E

This process relates to one for preparing the compound ($II_f$) by introducing a protective group into the amino function the compound ($II_e$).

As stated hereinabove, it is to be understood that said protected group is introduced to the amino function in order to prevent undesired side reaction which may take place in acylation of 3-amino-2-azetidizone compound with the compound ($II_e$) as an acylating agent for the preparation of 3-acylamino-3-azetidinone compound and followingly in order to easily split off said introduced protective group without any side reaction from the amino function to provide 3-acylamino-2-azetidinone compound which bears free amino function in the acyl group, e.g. Nocardicin A, in a mild reaction condition.

The protecting agent for amino includes organic carboxylic, sulfonic and carbonic acids, which are composed of the same protective group in the protected amino as explained for the protected amino for $R^2$ of the compound (I), and their reactive derivatives and more particularly an aliphatic carboxylic acid, an aromatic carboxylic acid and the corresponding sulfonic, and carbonic acids thereto, and their reactive derivatives.

The reactive derivatives include conventional ones such as acid halides, activated amides, activated esters, acid azides and the like.

When a free acid form of such protecting agent is employed, the reaction is preferably carried out in the presence of a condensing agent conventionally used in chemical synthesis of amino acid or peptide field.

This reaction is preferably carried out in the presence of a base, preferred examples of which include the same as those given in the explanation for Process 2.

The reaction is usually carried out in a conventional solvent, examples of which include water, acetone, methanol, ethanol, dioxane, tetrahydrofuran, N,N-dimethylformamide, pyridine, chloroform, dichloromethane, carbon tetrachloride, ethyl acetate, and the mixture thereof, and under mild conditions such as under cooling or at a somewhat elevated temperature.

The protective group thus introduced into the amino of the compound ($II_e$), is the same ones as given in the explanation for $R^2$ of compound (I), and accordingly preferred examples of the protective group are to be referred to said explanation.

Preparation F

This process relates to one for preparing the compound ($II_h$) by introducing a protective group into the carboxy group of the compound ($II_g$).

It is to be understand that the protective group is the same as those protective moiety in the protected carboxy given in the explanation of protected carboxy for $R_1$ of the compound (I).

The protecting agent for introducing a protective group into the carboxy group used in this preparation includes a conventional esterifying agent. Preferred examples of said esterifying agent may include a halide compound such as alkyl halide (e.g., methyl iodide, ethyl bromide, ethyl iodide, propyl bromide, etc.), an alkenyl or alkynyl halide (e.g., allyl bromide, propynyl bromide, etc.); substituted alkyl halide such as alkanoyloxyalkyl halide (e.g., acetoxymethyl chloride, acetoxyethyl chloride acetoxypropyl bromide, etc.), aroylalkyl halide (e.g., phenacyl bromide, etc.), an aralkyl halide (e.g., benzyl chloride, phenethyl chloride) and the like;

a dialkyl sulfate (e.g., dimethyl sulfate, diethyl sulfate, dipropyl sulfate, etc.);

an alkyl sulfonate (e.g., methyl benzenesulfonate, methyl p-toluenesulfonate, ethyl 4-bromobenzenesulfonate, etc.);

a haloformate such as alkyl haloformate (e.g., methyl chloroformate, ethyl chloroformate, propyl chloroformate, etc.), alkenyl or alkynyl haloformate (e.g., allyl chloroformate, propynyl chloroformate, etc.);

a diazoalkane (e.g., diazomethane, diazoethane, etc.) and;

a hydroxy compound such as alcohol, for example, an alkanol (e.g., methanol, ethanol, propanol, 2-chloroethanol, 2,2,2-trichloroethanol, butanol, 1-cyclopropylethanol, etc.), a cycloalkanol (e.g., cyclopropanol, cyclopentanol, cyclohexanol, borneol, adamantanol, etc.) and an aralkanol (e.g., benzyl alcohol, diphenylmethanol, phenethyl alcohol, etc.); and the like.

This reaction is preferably carried out in the presence of a base, preferred examples of which may include the same as those given in the explanation for Process 2.

In case that the hydroxy compound is used as an esterifying agent, the reaction is preferably carried out in the presence of a condensing agent conventionally used in a reaction of esterification, including dehydrating agent such as an acid (e.g. hydrochloric acid, sulfuric acid, etc.), such as N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N'-carbonylbis(2-methylimidazole), pentamethyleneketene-N-cyclohexylimine, diphenylketene-N-cyclohexylimine, alkoxyacetylene, 1-alkoxy-1-chloroethylene, 6-chloro-1-(4-chlorobenzenesulfonyloxy)-1H-benzotriazole, trialkyl phosphite, ethyl polyphosphate, isopropyl polyphosphate, phosphorus oxychloride, phosphorus trichloride, thionyl chloride, oxalyl chloride, triphenylphosphine, 2-ethyl-7-hydroxybenzisoxazolium salt, 2-ethyl-5-(m-sulfophenyl)isoxazolium hydroxide, (chloromethylene) dimethylammonium chloride, 2,2,4,4,6,6-hexachloro-1,3,5,2,4,6-triazatriphosphorine, or a mixed condensing agent such as triphenylphosphine and either carbon tetrahalide (e.g. carbon tetrachloride, carbon tetrabromide, etc.) or halogen (e.g. chlorine, bromine, etc.), and the like.

The reaction is usually carried out under cooling or at an elevated temperature.

RESOLUTION OF RACEMATE

It is well understood that the object substituted phenylacetic acid compound (I) which bears protected carboxy for $R^1$ and protected amino function $R^2$ in the terminal asymmetric carbons includes optical isomers, i.e. d-, l- and dl- isomers, and that the configuration at this asymmetric carbon atom of useful antibiotic Nocardicin A exists in d-configuration. Therefore, for the synthetic preparation of Nocarbicin A, it is important to prepare the optically active substituted phenylacetic acid compound especially the compound of the formula:

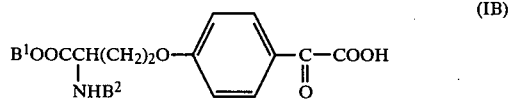

(IB)

wherein $B^1$ and $B^2$ are each protective group, which is the acylating agents for synthesizing Nocarbicin A. Although resolution of the compound (IB) per se may be achieved by a conventional method such as enzymatic or chemical reaction of the racemate of (IB), it is much more convenient and preferable to conduct such resolution antecedently to the oxidative preparation of the compound ($I_a$) by Process 1. For this purpose, preferred resolution methods will be illustrated in the following.

An optically active isomer of starting acetophenone compound (II$^l$) wherein both $R^1$ and $R^2$ are provided other than hydrogen, can be conveniently prepared first by resolving chemically or enzymatically a racemate of corresponding amino and/or carboxy acetophenone compounds of the formula:

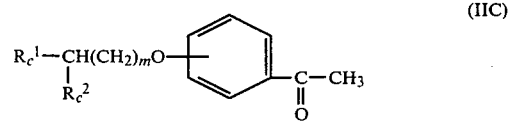

(IIC)

wherein
$R_c^1$ is carboxy or protected carboxy and
$R_c^2$ is amino or protected amino, and
then, if necessary, protecting the carboxy and/or amino function of the resolved optically active isomer of (IIC), according to the above illustrated Preparations E and/or F, correspondingly, Chemically resolution is usually conducted in well-known conventional manner, for example, (i) by reacting the racemic compound of the formula (IIC) with an optically active acid or base to provide corresponding diastereoisomeric salts, (ii) resolving them into two diastereoisomeric salts by conventional method such as fractional recrystallization and then (iii) followed by transforming the salt into each antipode of the compound (IIC) in usual manner.

Enzymatic resolution is conducted in an usual manner, for example, by incubating the racemate in the presence of an enzyme such as acylase or its enzyme preparation including microbial per se and the like, and then isolating the desired optically active isomer from the incubated mixture in a conventional manner.

Preferred examples of an enzyme to be employed in this process, may include an acylase such as Takadiasterse (trade mark made by Sankyo Co., Ltd.) and the like.

As previously mentioned, the object compounds, substituted phenylacetic acid compounds (I) are useful as starting acylating agents for preparing 3-acylamino-2-azetidinone, especially Nocardicin A, from 3-amino-2-azetidinone, and in this regard more detailed explanations are given as follows.

The preferred object compound (I) of this invention may be classified to two types of compounds in view of the starting acylating agent useful for the preparation of Nocardicin A, for a convenience's sake of explanation as follows.

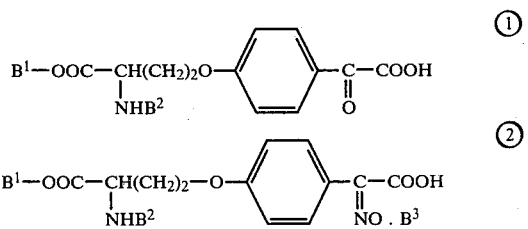

wherein $B^1$, $B^2$ and $B^3$ are each protective group as mentioned hereinabove.

Fundamental synthetic processes of Nocardicin A by acylating 3-amino-2-azetidinone compound (VI) are shown by the following reaction scheme.

(1) Preparation by using type ① of the compound as an acylating agent:

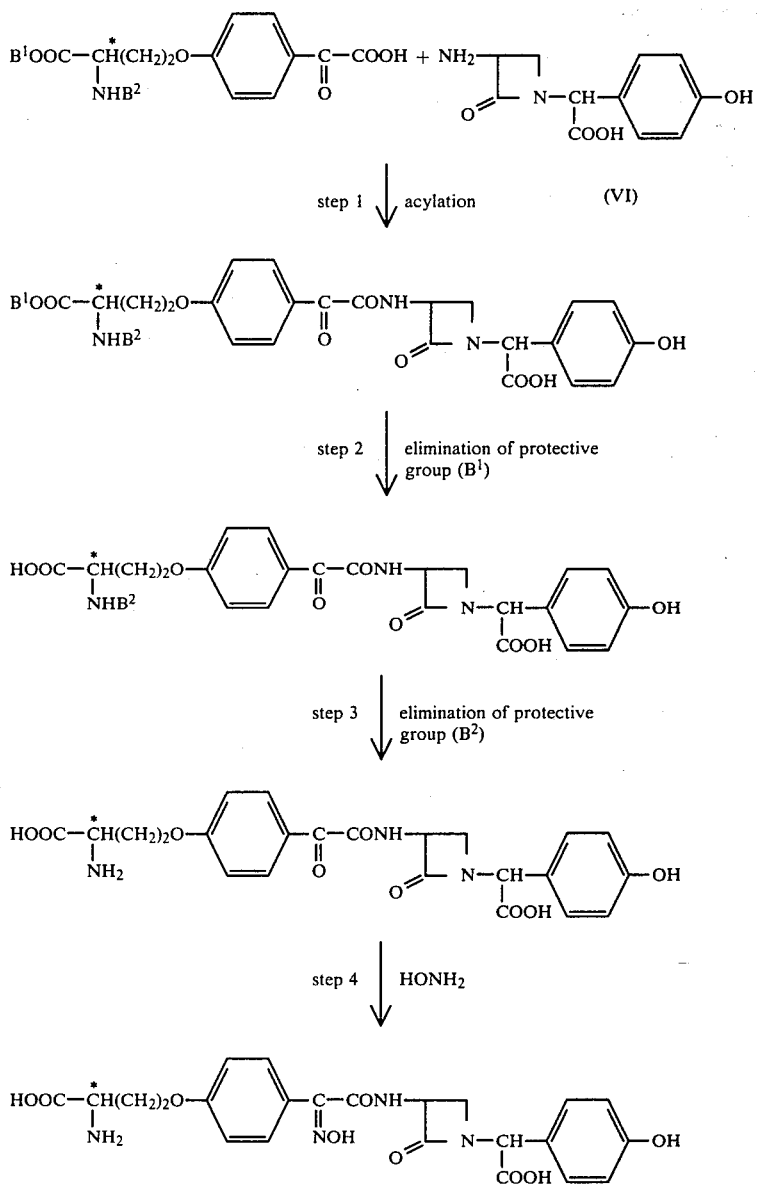
(Nocardicin A)
*Note: This refers to D-configuration.
(2) Preparation by using type ② of the compound as an acylating agent:
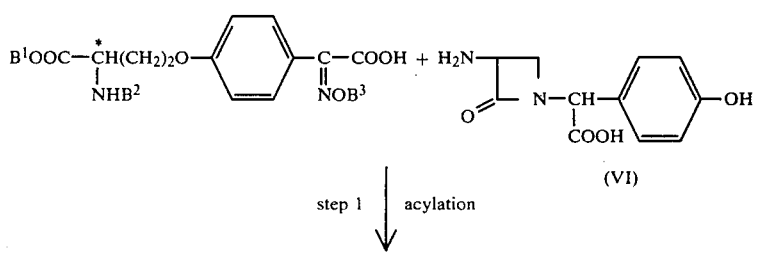

-continued

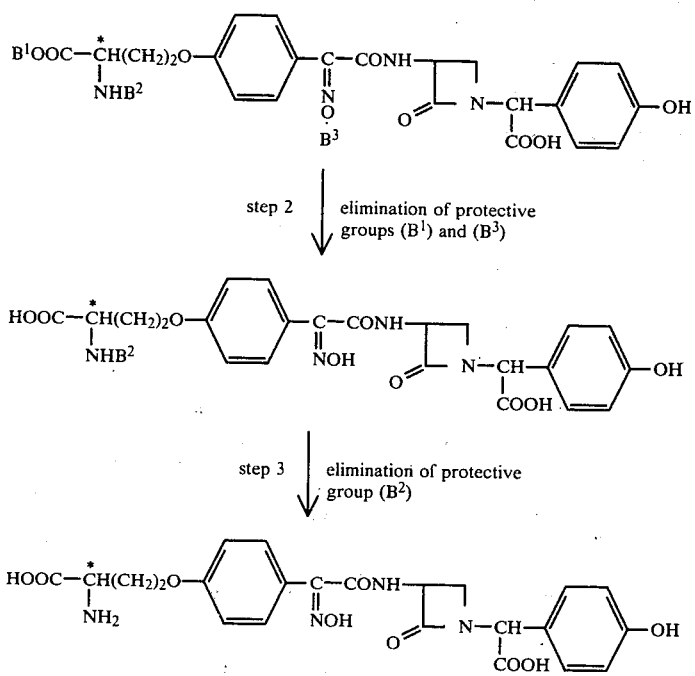

(Nocardicin A)

*Note: This refers to D-configuration

As far as available working examples are concerned, it is noted that type ① of the compound is more desirable starting acylating agent than type ② of the compound for preparing Nocardicin A, the reasons of which are as follows:

(a) In the process using type ② of the compound, the reaction may proceed by accompanying with geometrical isomerization of the α-hydroxyimino moiety of 3-acyl group in the elimination process (Step 1) of protective groups at the carboxy and hydroxyimino (i.e. $B^1$ and $B^3$) due to the fact that the reaction of this step is needed to be conducted under rathar severe conditions such as in the presence of a strong base such as sodium hydroxide or a strong acid such as hydrochloric acid in order to sufficiently eliminate the protective groups (i.e. $B^1$ and $B^3$).

Therefore, in proportion of such isomerization, not only the yield and purity of Nocardicin A decreases but also the purification of Nocardicin A become troublesome.

(b) On the other hand, the process using type ① of the compound comprises the said formation of hydroxyimino function in the last step, that is, the hydroxyimino function is directly formed, and accordingly and troublesome as mentioned above, does not occur.

The object compound (I) of this invention is also useful as a starting acylating agent for preparing the following compounds, new synthetic antibiotics, besides Nocardicin A.

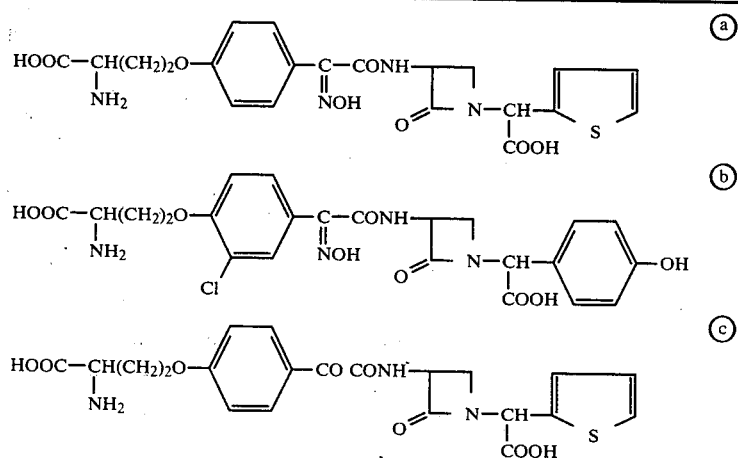

-continued (d)

HOOC—CH(CH₂)₂O—⟨C₆H₄⟩—CO—CONH—[β-lactam]—N—CH—⟨C₆H₄⟩—OH
        |                                              |
        NH₂                                          COOH MIC (Minimum Inhibitory Concentration) value
determined by conventional method

| Compound | Pseudomonas aeruginosa 10490 | Escherichia coli 50 | Escherichia coli 114 |
|---|---|---|---|
| ⓐ | 4 | 0.5 | |
| ⓑ | | | 8 |
| ⓒ | | 0.25 | 0.5 |
| ⓓ | 25 | | 1.6 |

Following examples are given for the purpose of illustrating this invention.

EXAMPLE 1

Methyl D,L-2-tert-butoxycarbonylamino-4-(4-acetylphenoxy)butyrate (17.6 g.) was dissolved in pyridine (75 ml.). To the resultant solution was added selenium dioxide (9.43 g.) at 80°~85° C. in the course of 30 minutes. After stirring at the same temperature for 3 hours, pyridine was distilled off from the reaction mixture under reduced pressure, and the residue was dissolved in aqueous solution of sodium bicarbonate. The resultant aqueous solution was washed successively with 100 ml. and 50 ml. of diethylether. After adjusting to pH 3~4 with 2 N hydrochloric acid under ice-cooling, it was extracted with ethylacetate. The extract was washed with a saturated aqueous solution of sodium chloride and dried over magnesium sulfate. This solution was treated with an activated carbon, and then ethylacetate was distilled off from the filtrate under reduced pressure. The resultant oily residue (21 g.) was crystallized with diisopropylether and subjected to post-treatment to give D,L-4-(3-tert-butoxycarbonylamino-3-methoxycarbonylpropoxy)phenylglyoxylic acid (11.7 g.), mp. 100°~102° C. (decomp.).

EXAMPLE 2

Methyl D-2-tert-butoxycarbonylamino-4-(4-acetylphenoxy)butyrate (0.70 g.) and selenium dioxide (0.50 g.) were treated in pyridine (4 ml.) in the substantially same way as described in Example 1 to give D-4-(3-tert-butoxycarbonylamino-3-methoxycarbonylpropoxy)-phenylglyoxylic acid (0.65 g.).

N.M.R. Spectrum (internal standard: tetramethylsilane)

| δppm (CDCl₃): | |
|---|---|
| 2.32 | (2H,q) |
| 3.77 | (3H,s) |
| 4.17 | (2H,t) |
| 4.52 | (1H,m) |
| 7.54 | (4H,AB-q,J = 9Hz) |

EXAMPLE 3

4-Methoxybenzyl D,L-2-tert-butoxycarbonylamino)-4-(4-acetylphenoxy)butyrate (3.40 g.) was dissolved in pyridine (15 ml.). Selenium dioxide (1.41 g.) was added thereto at 85° C. in the course of about 45 minutes. After stirring at 85°~90° C. for 4.5 hours, the reaction mixture was condensed to dryness, and the residue was dissolved in 5% aqueous solution of sodium bicarbonate. The resultant aqueous solution was filtered and the filtrate was washed with ethylacetate. The aqueous layer was adjusted to pH 2 with dil. hydrochloric acid and extracted with ethylacetate. The extract was washed with water and dried over magnesium sulfate. The solvent was distilled off to give 4-[3-tert-butoxycarbonylamino-3-(4-methoxybenzyloxycarbonyl)propoxy]phenylglyoxylic acid (3.40 g.).

I.R. Spectrum
$\nu cm^{-1}$ (liquid film): 3350, 1740, 1710, 1670

N.M.R. Spectrum (internal standard: tetramethylsilane)

| δppm (CDCl₃): | |
|---|---|
| 1.47 | (3H,s) |
| 2.29 | (2H,m) |
| 3.80 | (3H,s) |
| 4.13 | (1H,t,J = 7Hz) |
| 4.53 | (1H,d,J = 8Hz) |
| 5.13 | (1H,s) |
| 5.43 | (1H,m) |
| 6.76~8.20 | (8H,m) |
| 8.68 | (1H,broad s) |

EXAMPLE 4

To pyridine solution (10 ml.) containing 4-methoxybenzyl D-4-(4-acetylphenoxy)-2-tert-butoxycarbonylaminobutyrate (2.0 g.) was added selenium dioxide (0.880 g.) at 80°~85° C. in the course of about 20 minutes. After stirring at 85° C. for 4.5 hours, the reaction mixture was condensed under reduced pressure. 5% Aqueous solution of sodium bicarbonate was added to the residue, and then the aqueous solution was separated by decantation. The aqueous solution was washed with ethylacetate, adjusted to pH 2 with dil. hydrochloric acid, and extracted with ethylacetate. The extract was washed with water and dried over magnesium sulfate. The solvent was distilled off from the above solution under reduced pressure to give D-4-[3-tert-butoxycarbonylamino-3-(4-methoxybenzyloxycarbonyl)propoxy]phenylglyoxylic acid (2.20 g.).

I.R. Spectrum $\nu cm^{-1}$ (liquid film): 3350, 1740, 1710, 1670,

N.M.R. Spectrum (internal standard: tetrmethylsilane)

| δppm (CDCl₃): | |
|---|---|
| 1.47 | (3H,s) |
| 2.29 | (2H,m) |

-continued

| δppm (CDCl₃): | |
|---|---|
| 3.80 | (3H,s) |
| 4.13 | (1H,t,J = 7Hz) |
| 4.53 | (1H,d,J = 8Hz) |
| 5.13 | (1H,s) |
| 5.43 | (1H,m) |
| 6.76~8.20 | (8H,m) |
| 8.68 | (1H,broad s) |

EXAMPLE 5

D,L-4-[3-tert-Butoxycarbonylamino-3-(4-methoxybenzyloxycarbonyl)propoxy]phenylglyoxylic acid (2.84 g.) was dissolved in 50% methanol-aqueous solution (30 ml.). To the resultant solution were successively added hydroxylamine hydrochloride (0.65 g.) and magnesium hydroxide (1.37 g.). After stirring at ambient temperature over one night, methanol was distilled off from the reaction mixture under reduced pressure, and the residual liquid was adjusted to pH 2 with dil. hydrochloric acid. This aqueous solution was extracted with ethylacetate. The extract was washed with water, dreid over magnesium sulfate, and condensed to dryness under reduced pressure to give D,L-2-[4-{3-tert-butoxycarbonylamino-3-(4-methoxybenzyloxycarbonyl)propoxy}phenyl]-2-hydroxyiminoacetic acid (2.75 g.).

I.R. Spectrum νcm⁻¹ (liquid film): 3450~3300, 1720, 1710

N.M.R. Spectrum

| δppm (CDCl₃): | |
|---|---|
| 1.42 | (9H,s) |
| 2.22 | (2H,m) |
| 3.73 | (3H,s) |
| 3.97 | (2H,t,J = 5Hz) |
| 4.50 | (1H,m) |
| 5.10 | (2H,s) |
| 5.58 | (1H,broad s) |
| 6.67~7.86 | (8H,m) |
| 10.00 | (1H,s) |

EXAMPLE 6

D,L-2-[4-{3-tert-Butoxycarbonylamino-3-(4-methoxybenzyloxycarbonyl)propoxy}phenyl]-2-hydroxyiminoacetic acid (0.502 g.) was dissolved in dichloromethane (5 ml.), and then benzoyl chloride (0.280 g.) was further added thereto at 20° C. Reaction was carried out at the same temperature for 5 hours. After reaction was over, dried petroleum ether (25 ml.) was poured to the reaction mixture to produce an oily substance. The solvent was removed off by decantation and the residual oily substance was changed to powder by treating with petroleum ether. Thus obtained powder was D,L-2-benzoyloxyimino-2-[4-{3-tert-butoxycarbonylamino-3-(4-methoxybenzyloxycarbonyl)propoxy}phenyl]acetic acid (0.350 g.).

I.R. Spectrum νcm⁻¹ (nujol): 3250, 1750, 1740~1710
N.M.R. Spectrum (internal standard: teramethylsilane)

| δppm [(CD₃)₂SO]: | |
|---|---|
| 1.35 | (9H,s) |
| 2.16 | (2H,m) |
| 3.73 | (3H,s) |
| 4.00~4.34 | (3H,m) |
| 5.08 | (2H,s) |
| 6.80~8.07 | (14H,m) |
| 8.62 | (1H,d,J = 5Hz) |
| 9.62 | (1H,s) |

EXAMPLE 7

D,L-2-[4-(3-tert-Butoxycarbonylamino-3-methoxycarbonylpropoxy)phenyl]-2-hydroxyiminoacetic acid (1.20 g.) was dissolved in a mixed solution (50 ml.) of dichloromethane and ethylacetate (volume ratio 1:2). To the resultant solution was added benzoyl chloride (0.90 g.). After stirring at ambient temperature for 48 hours, the reaction mixture was condensed under water-cooling and reduced pressure, and the residue was washed thrice with petroleum ether. The residue was crystallized with a mixed solution of diethylether and diisopropylether to give D,L-2-benzoyloxyimino-2-[4-(3-tert-butoxycarbonylamino-3-methoxycarbonylpropoxy)phenyl]acetic acid (620 mg.).

I.R. Spectrum νcm⁻¹ (nujol): 3350, 1750, 1730, 1720, 1710

EXAMPLE 8

Methyl DL-4-(m-acetylphenoxy)-2-tert-butoxycarbonylaminobutyrate (2.21 g.) was dissolved in pyridine (10 ml.), and to the solution was added selenium dioxide (1.11 g.), whereafter the solution was stirred at 90° C. for 4.5 hours. The reaction mixture was filtered and the filter cake was washed with ethyl acetate. These washings and the filtrate were combined and evaporated to dryness under reduced pressure to give a residue, which was poured into a mixture of an aqueous sodium bicarbonate and ethyl acetate. The insoluble materials were removed by filtration and the filtrate was adjusted to pH 2 with 10% hydrochloric acid. This aqueous solution was extracted twice with ethyl acetate, and the extract was washed with water and then dried over magnesium sulfate. The ethyl acetate was removed by evaporation from the solution under reduced pressure to give DL-m-(3-tert-butoxycarbonylamino-3-methoxycarbonylpropoxy)phenylglyoxylic acid (1.35 g.).

I.R. νcm⁻¹ (film): 3370, 1760, 1730, 1690, 1600.

EXAMPLE 9 p-(4-Methoxycarbonylpropoxy)phenylglyoxylic acid (2.43 g.) was obtained by reacting methyl 4-(p-acetylphenoxy)butyrate (3.83 g.) with selenium dioxide (3.05 g.) in pyridine (120 ml.) in substantially the same manner as that of Example 8.

m.p. 70°-73° C.

EXAMPLE 10 p-(3-Phthalimidopropoxy)phenylglyoxylic acid (4.01 g.) was obtained by reacting p-(3-phthalimidopropoxy)acetophenone (5.17 g.) with selenium dioxide (3.05 g.) in pyridine (120 ml.) in substantially the same manner as that of Example 8.

m.p. 159°-161° C.

I.R. νcm⁻¹ (Nujol): 1770, 1720 (shoulder), 1710, 1670, 1610.

EXAMPLE 11

DL-p-(3-tert-Butoxycarbonylamino-3-methoxycarbonylpropoxy)phenylglyoxylic acid (750 mg.) was dissolved in a mixture of chloroform (15 ml.) and methanol (10 ml.), and to the solution was added 1,3,5-trichloroisocyanuric acid (180 mg.) in the course of 5 minutes, whereafter the mixture was stirred at ambient temperature for 18.7 hours. The insoluble materials were filtered off from the reaction mixture and the filtrate was evaporated to dryness under reduced pressure. The resultant residue was dissolved in ethyl acetate, and the solution was washed with water and then dried over magnesium sulfate. This solution was evaporated to dryness under reduced pressure to give a residue, which was subjected to column chromatography on silica gel (11 g.). Elution was carried out with a mixture of chloroform and methanol (99:1 by volume) and the fractions containing a desired compound were collected. The solvent was removed by evaporation from the eluate under reduced pressure to give DL-p-(3-tert-butoxycarbonylamino-3-methoxycarbonylpropoxy)-3-chlorophenylglyoxylic acid (380 mg.).

I.R. $\nu cm^{-1}$ (film): 3410, 1740, 1720, 1700, 1680.

PREPARATION 1

4-Hydroxyacetophenone (21.2 g.) was dissolved in dried bis(2-methoxyethyl)ether (600 ml.), and 50% oily sodium hydride (6.25 g.) was added thereto. After stirring at ambient temperature for 30 minutes, D,L-2-oxo-3-phthalimidotetrahydrofuran (30 g.) was added thereto. This reaction mixture was refluxed for 6 hours. Then it was allowed to stand over one night and the solvent was evaporated to dryness under reduced pressure. After the residue was dissolved in water (150 ml.), the aqueous solution was washed twice with ethylacetate (100 ml.). To the aqueous solution was added 2 N hydrochloric acid untill a fresh deposite of a precipitate was not observed. Then, the resultant mixture was extracted with each 150 ml. and 100 ml. of ethylacetate. The ethylacetate layer was further extracted with once 100 ml. and twice 50 mls. of a saturated aqueous solution of sodium bicarbonate. The extract was washed with ethylacetate (150 ml.). To the above aqueous solution was added 2 N hydrochloric acid untill a fresh deposite of a precipitate was not observed, and then, sodium chloride was further added thereto. The aqueous solution was extracted with once 150 ml. and twice 100 mls. of ethylacetate. The extract was dried over magnesium sulfate. The ethylacetate solution was treated with an activated carbon, and then, ethylacetate was distilled off under reduced pressure to give D,L-4-(4-acetylphenoxy)-2-phthalimidobutyric acid (50.5 g.), mp. 164°~166° C.

PREPARATION 2

To an anhydrous bis(2-methoxyethyl) ether solution (240 ml.) containing m-hydroxyacetophenone (7.48 g.) was added sodium hydride (50% mineral oil) (2.32 g.), and the mixture was stirred at ambient temperature for half an hour. To the resultant mixture was added 2-phthalimido-4-butanolide (9.24 g.), and the mixture was refluxed under heating for 5 hours. The reaction mixture was allowed to cool and then water (500 ml.) was added thereto. This aqueous solution was washed with ethyl acetate and adjusted to pH 2 with 10% hydrochloric acid, whereafter the solution was extracted with ethyl acetate. The extract was washed four times with water and then dried over magnesium sulfate. After the solution was treated with charcoal, the ethyl acetate was removed by evaporation from the solution under reduced pressure to give an oily residue (6.42 g.).

I.R. $\nu cm^{-1}$ (film): 1780, 1760, 1720, 1700, 1610.

The oily residue (7.8 g.) thus obtained was dissolved in a mixture of acetic acid (25 ml.), concentrated hydrochloric acid (58 ml.) and water (58 ml.), and then the mixture was refluxed under heating for three hours. After the reaction mixture was treated with charcoal, the filtrate was adjusted to pH 4 with concentrated ammonium hydroxide aqueous solution. This solution was evaporated to dryness under reduced pressure and the resultant residue was crystallized from methanol to give DL-4-(m-acetylphenoxy)-2-aminobutyric acid (0.81 g.). The mother liquor was evaporated to dryness under reduced pressure and the residue was crystallized from ethanol to give the same product (3.70 g.).

Total yield was 4.51 g.

m.p. 198°–201° C. (decomposition)

PREPARATION 3

Crude 4-(p-acetylphenoxy)butyric acid (1.66 g.) was obtained by reacting 4-butanolide (2.584 g.) with p-hydroxyacetophenone (1.36 g.) in the presence of sodium hydride (50% mineral oil) (480 mg.) in substantially the same manner as that of Preparation 1.

This product (1.5 g.) was recrystallized from methanol (15 ml.) to give the pure object compound (0.83 g.).

m.p. 149°–151° C.

I.R. $\nu cm^{-1}$ (Nujol): 3050, 1730, 1650, 1600.

PREPARATION 4

D,L-4-(4-Acetylphenoxy)-2-phthalimidobutyric acid (40 g.) was dissolved in ethylacetate under heating. To the solution were successively added, with stirring, water (300 ml.) and conc. hydrochloric acid (300 ml.). After refluxing for about 3.5 hours, water (about 100~150 ml.) was distilled off from the reaction mixture under reduced pressure, and then the residual solution was cooled. A solid material deposited in the above residual solution was isolated by filtration and washed with water. The filtrate and the wash water were put together, and then the solvent was evaporated to dryness under reduced pressure. The residue was dissolved in water (200 ml.) and treated with an activated carbon. The filtrate was condensed under reduced pressure, and conc. aqueous ammonia was added thereto to adjust pH 4. The resultant solution was allowed to stand over one night under cooling. A deposited crystal was isolated by filtration and washed successively with thrice water, twice acetone and twice diethylether, and then was dried to give D,L-2-amino-4-(4-acetylphenoxy)butyric acid (20.9 g.), mp. 193°~194° C. (decomp.).

PREPARATION 5

D,L-2-Amino-4-(4-acetylphenoxy)butyric acid (20.2 g.) and triethylamine (12.87 g.) were dissolved in a mixed solution of water (100 ml.) and dioxane (100 ml.). To the resultant solution was added 2-tert-butoxycarbonyloxyimino-2-phenylacetonitrile (23 g.). After stirring for 2 hours at ambient temperature, dioxane was distilled off from the reaction mixture under reduced pressure. The resultant aqueous solution was washed thrice with each ethylacetate (100 ml.). The wash solution was extracted twice with each 5% aqueous sodium bicarbonate solution (50 ml.). The extract and the above aqueous solution were put together. After the resultant aqueous solution was adjusted to pH 2~3 with 6 N hydrochloric acid, it was extracted with ethylacetate. The extract was washed with a saturated aqueous solution of sodium chloride, dried over magnesium slfate and treated with an activated carbon. Ethylacetate was removed off from the filtrate under reduced pressure. The oily residue was allowed to stand for a while under cooling, and a deposited crystal was treated with diethylether to give D,L-2-tert-butoxycarbonylamino-4-(4-acetylphenoxy)butyric acid (23.8 g.). The crystal (3 g.) was dissolved in a small amount of methanol and treated with an activated carbon. The filtrate was condensed to dryness under reduced pressure. The residue was recrystallized from diethylether and diisopropylether to give a pure crystal (2.5 g.), mp. 100°~101° C.

PREPARATION 6

Hydrochloric acid salt of methyl D,L-2-amino-4-(4-acetylphenoxy)butyrate (19.0 g.) and triethylamine (15.2 g.) were dissolved in 50% aqueous solution of dioxane (200 ml.). 2-tert-Butoxycarbonyloxyimino-2-phenylacetonitrile (19.5 g.) was added thereto. After stirring for 5 hours at ambient temperature, dioxane was distilled off frm the reaction mixture under reduced pressure. To the residual aqueous solution was added diethylether. An ether layer was separated and washed successively with 1% hydrochloric acid, 5% aqueous solution of potassium carbonate and water, and then dried over magnesium sulfate. After treating with an activated cabon, the filtrate was condensed to about 25 ml.. n-Hexane was added thereto, and the resultant solution was allowed to stand. A crystal deposited in the solution was isolated by filtration to give methyl D,L-2-tert-butoxycarbonylamino-4-(4-acetylphenoxy)-butyrate (15.9 g.), mp. 93°~94° C.

PREPARATION 7

D,L-2-tert-Butoxycarbonylamino-4-(4-acetylphenoxy)butyric acid (12.8 g.) and cinchonidine (10.2 g.) were dissolved in acetonitrile (300 ml.) under warming. The resultant solution was treated with an activated carbon, and the filtrate was allowed to stand over one night. Deposited gel-state crystal was separated by filtration and washed with dithylether (300 ml.). To the crystal (12.08 g.) was added acetonitrile (150 ml.). The resultant solution was allowed to stand over one night. After recrystallization, a crystal was washed with diethylether (200 ml.). Allowing to stand over one night, the above crystal was further recrystallized, and then washed with diethylether. The resultant crystal (7.84 g.) was still further recrystallized from acetonitrile (160 ml.) and washed with diethylether (200 ml.) to give cinchonidine salt of L-2-tert-butoxycarbonylamino-4-(4-acetylphenoxy)butyric acid (6.52 g.), m.p. 144°~147° C., $[\alpha]_D = -64.1°$ (solvent: methanol C=2.2).

While, the filtrate which is obtained by filtration of the above-mentioned gel-state crystal was condensed to about 100 ml. under reduced pressure. After standing over one night, a deposited crystal (7.90 g.) was further recrystallized allowing to stand over one night. The resultant crystal (6.67 g.) was still further recrystallized from acetonitrile (70 ml) in the same way as mentioned above to give cinchonidine salt of D-2-tert-butoxycarbonylamino-4-(4-acetylphenoxy)butyric acid (5.66 g.), mp. 130°~133° C., $[\alpha]_D = -77.5°$ (solvent: methanol C=2.0).

Thus obtained cinchonidine salt of D-2-tert-butoxycarbonylamino-4-(4-acetylphenoxy)butyric acid (5.00 g.) was dissolved in chloroform (50 ml.). With stirring 5% hydrochloricacid was added thereto to adjust pH 2. A chloroform layer was isolated by filtration and the above-mentioned operations were repeated again. A chloroform layer was dried over magnesium sulfate and the solvent was distilled off under reduced pressure. The resultant oily residue was crystallized with diethylether and treated with diisopropylether to give D-2-tert-butoxycarbonylamino-4-(4-acetylphenoxy)-butyric acid (2.40 g.), mp. 90°~92° C., $[\alpha]_D = +8.1°$ (solvent: methanol C=2.0).

While, cinchonidine salt of L-2-tert-butoxycarbonylamino-4-(4-acetylphenoxy)butyric acid (5.50 g.) was treated in the same way as mentioned above to give L-2-tert-butoxycarbonylamino-4-(4-acetylphenoxy)-butyric acid (2.88 g.), mp. 90°~92° C., $[\alpha]_D = -8.5°$ (solvent: methanol C=2.0).

PREPARATION 8

DL-4-(m-Acetylphenoxy)-2-aminobutyric acid (4.30 g.), 2-tert-butoxycarbonyloxyimino-2-phenylacetonitrile (4.92 g.) and triethylamine (2.53 g.) were dissolved in a mixture of dioxane (22 ml.) and water (22 ml.), whereafter the mixture was stirred at ambient temperature for 2.5 hours. The dioxane was removed by evaporation from the reaction mixture under reduced pressure to give an aqueous solution which was adjusted to pH 8-9 with an aqueous sodium bicarbonate. The resultant aqueous solution was washed with ethyl acetate and adjusted to pH 2 with 10% hydrochloric acid under ice-cooling. This solution was extracted three times with ethyl acetate, and the extract was washed with water and then dried over magnesium sulfate. The solvent was removed by evaporation from the solution under reduced pressure to give DL-4-(m-acetylphenoxy)-2-tert-butoxycarbonylaminobutyric acid (2.03 g.).

I.R. $\nu$ cm$^{-1}$ (film): 3350, 2600 (broad), 1760, 1730, 1700, 1600.

PREPARATION 9

D,L-2-Amino-4-(4-acetylphenoxy)butyric acid (18.6 g.) was dissolved in methanol (90 ml.). Methanol solution (180 ml.) containing hydrogen chloride (31.5 g.) was added thereto. After stirring at 55°~60° C. for 2.5 hours, the reaction mixture was treated with an activated carbon. Methanol was distilled off from the filtrate under reduced pressure. The resultant oily residue (27.8 g.) was crystallized with a mixed solution of acetonitrile (35 ml.) and benzene (20 ml.). The crystal and the above mixture solution were allowed to stand for about 60 hours in a refrigerator and then the crystal was isolated by filtration to give hydrochloric acid salt of methyl D,L-2-amino-4-(4-acetylphenoxy)butyrate (19.0 g.), m.p. 98°~108° C.

I.R. Spectrum $\nu$cm$^{-1}$ (nujol): 1750, 1680, 1600

PREPARATION 10

D,L-2-tert-Butoxycrbonylamino-4-(4-acetylphenoxy)butyric acid (20.2 g.) was dissolved in methanol (100 ml.). A mixed solution of diethylether and ethanol which contained diazomethane was dropwise added thereto at 5° C. with stirring, untill color of diazomethane did not disappear. The reaction mixture was condensed to dryness under reduced pressure and the resultant oily residue was dissolved in diethylether. n-Hexane was added thereto. After allowing to stand over one night, a crystal deposited in the solution was isolated by filtration to give methyl D,L-2-tert-butoxycarbonylamino-4-(4-acetylphenoxy)butyrate (19.1 g.). This crystal (1 g.) was dissolved in a small amount of methanol and treated with an activated carbon. The filtrate was condensed to dryness. The residue was recrystallized from a mixture of ethanol (30 ml.) and n-hexane (15 ml.) to give a purified crystal (760 mg.), mp. 93°~94° C.

PREPARATION 11

D-2-tert-Butoxycarbonylamino-4-(4-acetylphenoxy)-butyric acid (2.10 g.) was dissolved in ethylacetate 15 ml.. A diethylether solution containing diazomethane was dropwise added thereto under ice-cooling, untill color of diazomethane did not disappear. After stirring at the same temperature for one hour, the solvent was distilled off from the reaction mixture under reduced pressure. The residue was crystallized with diisopropylether and post-treated to give methyl D-2-tert-butoxycarbonylamino-4-(4-acetylphenoxy)butyrate (2.02 g.), mp. 81°~82° C., $[\alpha]_D = +18.2°$ (solvent: methanol C=1.9).

PREPARATION 12

L-2-tert-Butoxycarbonylamino-4-(4-acetylphenoxy)-butyric acid (2.60 g.) was treated in the substantially same way as described in Preparation 11 to give methyl L-2-tert-butoxycarbonylamino-4-(4-acetylphenoxy)butyrate (2.56 g.), mp 81°~82° C., $[\alpha]_D = -16.0°$ (solvent: methanol C=1.9).

PREPARATION 13

D,L-2-tert-Butoxycarbonylamino-4-(4-acetylphenoxy)butyric acid (3.36 g.) was suspended in dichloromethane (30 ml.). Under ice-cooling, triethylamine (1.51 g.) was further added to be dissolved therein. To the resultant solution, under ice-cooling, was dropwise added dichloromethane solution (10 ml.) containing 4-methoxybenzylbromide (3.02 g.) with stirring in the course of 15 minutes. After stirring for further 3.5 hours, the reaction was condensed under reduced pressure. The residue was dissolved in ethylacetate. The resultant solution was successively washed with dil. hydrochloric acid, water, 5% aqueous solution of sodium bicarbonate and water, and then dried over magnesium sulfate. This solution was then condensed to dryness under reduced pressure. This residue was crystallized with petroleum ether and isolated by filtration to give 4-methoxybenzyl D,L-2-tert-butoxycarbonylamino-(4-(4-acetylphenoxy)butyrate (1.85 g.), mp. 67°~71° C.

I.R. Spectrum $\nu cm^{-1}$ (nujiol): 3375, 1745, 1695, 1680

PREPARATION 14

To dichloromethane solution (40 ml.) containing D-4-(4-acetylphenoxy)-2-tert-butoxycarbonylaminobutyric acid (3.36 g.) was added triethylamine (1.81 g.) under ice-cooling. 4-Methoxybenzylbromide (3.624 g.) was further added thereto, and the resultant solution was stirred for one hour at the same temperature and over one night at ambient temperature. The reaction mixture was condensed under reduced pressure, and the residue was dissolved in ethylacetate. The resultant ethylacetate solution was successively washed with 5% aqueous solution of sodium bicarbonate, water, dil. hydrochloric acid and water, and then dried over magnesium sulfate. The solvent was distilled off from the solution under reduced pressure. The resultant residue was crystallized with petroleum ether to give 4-methoxybenzyl D-4-(4-acetylphenoxy)-2-tert-butoxycarbonylaminobutyrate (2.80 g.), mp 69°~71° C.

PREPARATION 15

DL-4-(m-Acetylphenoxy)-2-tert-butoxycarbonylaminobutyric acid (2.03 g.) was dissolved in ethyl acetate (30 ml.), and to the solution was added dropwise an ether solution of diazomethane with stirring under ice-cooling until the color of the diazomethane was appeared. After the stirring was continued at the same temperature for additional half an hour, the reaction mixture was evaporated to dryness under reduced pressure to give methyl DL-4-(m-acetylphenoxy)-2-tert-butoxycarbonylaminobutyrate (2.21 g.).

I.R. $\nu$ cm$^{-1}$ (film): 3370, 1760, 1730, 1700, 1600.

PREPARATION 16

4-(p-Acetylphenoxy)butyric acid (4.1 g.) was suspended in ethyl acetate (80 ml.), and to the suspension was added dropwise an ether solution of diazomethane with stirring under ice-cooling until a color of the diazomethane was appeared. After the stirring was continued at the same temperature for additional half an hour, a small amount of acetic acid was added to the reaction mixture, and then the solution was stirred for a while. This solution was evaporated to dryness under reduced pressure and the residue was treated with a mixture of isopropyl ether and n-hexane (1:1 by volume) to give methyl 4-(p-acetylphenoxy)butyrate (3.83 g.). m.p. 53°-54° C.

I.R. $\nu$ cm$^{-1}$ (Nujol): 1730, 1670, 1610.

PREPARATION 17

D-4-(3-Amino-3-carboxypropoxy)phenylglyoxylic acid (134 mg.) was dissolved in water (6 ml.) containing sodium carbonate (41 mg.). To the resultant solution was added hydroxylamine hydrochloride (28 mg.). After refluxing for about 20 minutes, dil. hydrochloric acid was added thereto to adjiust pH 2. A deposited crystal was isolated by filtration. This crystal was recrystallized from water to give D-2-[4-(3-amino-3-carboxypropoxy)phenyl]-2-hydroxyiminoacetic acid (100 mg.), mp. 193°~194° C. (decomp.).

PREPARATION 18

D,L-4-(3-tert-butoxycarbonylamino-3-methoxycarbonylpropoxy)phenylglyoxylic acid (1.91 g.) was dissolved in a mixed solution of methanol (32 ml.) and water (8 ml.). In the resultant solution was suspended hydroxylamine hydrochloride (0.426 g.) and magnesium hydroxide (0.870 g.). After stirring for 18 hours at ambient temperature, the reaction mixture was subjected to filtration. The filtrate was condensed under water-cooling and reduced pressure. The condensed solution was adjusted to pH 2 with dil. hydrochloric acid and extracted with ethylacetate. The extract was washed with water and then dried over magnesium sulfate. This solution was condensed to dryness under reduced pressure, and the residue was crystallized with diethylether to give D,L-2-[4-(3-tert-butoxycarbonylamino-3-methoxycarbonylpropoxy)phenyl]-2-hydroxyiminoacetic acid (1.54 g.), mp. 132°~134° C.

I.R. Spectrum $\nu cm^{-1}$ (nujol): 3400, 3290, 1720, 1695

N.M.R. Spectrum (internal standard: tetramethylsilane)

| $\delta$ ppm [(CD$_3$)$_2$CO]: | |
|---|---|
| 1.40 | (9H,s) |
| 2.27 | (2H,m) |

-continued

| δppm [(CD₃)₂CO]: | |
|---|---|
| 3.70 | (3H,s) |
| 4.16 | (2H,t,J = 5Hz) |
| 4.37 | (1H,m) |
| 4.53 | (1H,broad s) |
| 6.98, 7.55 | (2H,AB-q,J = 9Hz) |

PREPARATION 19 p-Hydroxyacetophenone (13.6 g.), 1,3-dibromopropane (121.2 g.) and potassium carbonate (15.8 g.) were dissolved in acetone (250 ml.), and the solution was refluxed under heating for 6 hours. After the reaction mixture was filtered, the acetone was removed by evaporation from the filtrate under reduced pressure to give an oily residue. The excess of 1,3-dibromopropane was removed by distillation from the oily residue under reduced pressure to give a residue, which was subjected to column chromatography on silica gel (20 g.). Elution was carried out with benzene and the fractions containing a desired compound were collected. The eluate was evaporated to dryness under reduced pressure to give p-(3-bromopropoxy)acetophenone (18 g.).

I.R. νcm⁻¹ (film): 1675, 1600.

N.M.R. δ ppm (CCl₄): 2.28 (2H, m), 2.39 (3H, s), 3.32 (2H, t, J=7 Hz), 4.07 (2H, t, J=7 Hz), 6.80 (2H, d, J=8 Hz), 7.76 (2H, d, J=8 Hz)

PREPARATION 20 p-(3-Bromopropoxy)acetophenone (5.14 g.) and potassium phthalimide (3.75 g.) were dissolved in anhydrous N,N-dimethylformamide (50 ml.), and the solution was stirred at 70° C. for 2.5 hours. After the reaction mixture was allowed to cool, water (300 ml.) was poured thereto. The aqueous solution was extracted three times with ethyl acetate, and the extract was washed with ethyl acetate and then dried over magnesium sulfate. The ethyl acetate was removed by evaporation from the solution under reduced pressure, and the resultant residue was treated with ether to give p-(3-phthalimidopropoxy)acetophenone (5.75 g.).

m.p. 138°-141° C.

I.R. ν cm⁻¹ (Nujol): 1770, 1720 (shoulder), 1710, 1670, 1610.

N.M.R. δ ppm (CDCl₃): 2.20 (2H, m), 2.49 (3H, s), 3.89 (2H, t, J=7 Hz), 4.05 (2H, t, J=7 Hz), 6.76 (2H, d, J=8 Hz), 7.77 (6H, m)

What we claim is:

1. A compound of the formula:

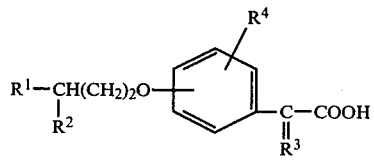

wherein
R¹ is an alkoxycarbonyl or, substituted or unsubstituted aralkoxycarbonyl,
R² is alkoxycarbonylamino,
R³ is oxo, hydroxyimino or aroyloxyimino, and
R⁴ is hydrogen or halogen.

2. A compound according to claim 1, wherein
R¹ is methoxycarbonyl or p-methoxybenyloxycarbonyl,
R² is tert-butoxycarbonylamino, and
R³ is oxo.

3. A compound according to claim 2 wherein R¹ is methoxycarbonyl.

4. A compound according to claim 1 wherein R⁴ is halogen.

5. A compound according to claim 1, wherein R⁴ is hydrogen.

6. A compound according to claim 5, wherein R³ is hydroxyimino or aroyloxyamine.

7. A compound according to claim 6, wherein said aroyloxyamine is benzoyloxyamino.

* * * * *